(12) United States Patent
Ogawa

(10) Patent No.: US 8,085,405 B2
(45) Date of Patent: Dec. 27, 2011

(54) DETECTING ELEMENT, AND TARGET SUBSTANCE DETECTING DEVICE AND METHOD OF DETECTING TARGET SUBSTANCE USING THE SAME

(75) Inventor: Miki Ogawa, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 411 days.

(21) Appl. No.: 12/160,987

(22) PCT Filed: Mar. 13, 2007

(86) PCT No.: PCT/JP2007/055586
§ 371 (c)(1),
(2), (4) Date: Jul. 15, 2008

(87) PCT Pub. No.: WO2007/108453
PCT Pub. Date: Sep. 27, 2007

(65) Prior Publication Data
US 2010/0195106 A1      Aug. 5, 2010

(30) Foreign Application Priority Data

Mar. 16, 2006   (JP) .................................. 2006-072587

(51) Int. Cl.
*G01N 21/55* (2006.01)
(52) U.S. Cl. ........ 356/445; 356/312; 356/318; 356/246; 422/52; 422/162; 422/172
(58) Field of Classification Search .......... 356/312–318, 356/445, 246; 422/52, 162, 172
See application file for complete search history.

(56) References Cited

U.S. PATENT DOCUMENTS

| | | | |
|---|---|---|---|
| 6,870,627 B2 * | 3/2005 | Elkind et al. ................. | 356/317 |
| 7,403,287 B2 * | 7/2008 | Ogawa et al. ................ | 356/445 |
| 2007/0105087 A1 | 5/2007 | Ban et al. | |
| 2008/0117423 A1 | 5/2008 | Ogawa et al. | |

FOREIGN PATENT DOCUMENTS

| | | |
|---|---|---|
| EP | 1445601 A2 | 8/2004 |
| JP | 2000035685 | 2/2000 |

OTHER PUBLICATIONS

PCT International Search Report and Written Opinion of the International Searching Authority, mailed Jun. 28, 2007, in PCT/JP2007/055586.

Byun, et al., "Investigation of the sensitivity enhancement of nanoparticle based surface plasmon resonance biosensors using rigorous coupled wave analysis", Proceedings of SPIE, vol. 5703, pp. 61-70, Mar. 2005, XP-002438124.

(Continued)

*Primary Examiner* — Gregory J Toatley
*Assistant Examiner* — Iyabo S Alli
(74) *Attorney, Agent, or Firm* — Fitzpatrick, Cella, Harper & Scinto

(57) ABSTRACT

A detecting element used for a detecting device for detecting a target substance in a sample by utilizing plasmon resonance. The detecting element includes a substrate and a plurality of metal members provided on the substrate, the metal member constituting a columnar structure and being oriented in a long axis direction thereof. The detecting element can improve sensitivity of the detecting device for detecting a target substance utilizing plasmon resonance.

10 Claims, 6 Drawing Sheets

OTHER PUBLICATIONS

Atkinson, et al., "Anisotropic optical properties of arrays of gold nanorods embedded in alumina", Physical Review, B, vol. 73, Jun. 5, 2006, pp. 235402-1-235402-8.

Enoch, et al., "Optical sensing based on plasmon coupling in nanoparticle arrays", Optics Express, vol. 12, No. 15, Jul. 26, 2004, pp. 3422-3427, XP-002438126.

Link, et al., "Simulation of the Optical Absorption Spectra of Gold Nanorods as a Function of Their Aspect Ratio and the Effect of the Medium Dielectric Constant", J. Phys. Chem. B, vol. 103, No. 16, 1999, pp. 3073-3077.

U.S. Appl. No. 12/162,789, filed Jul. 30, 2008, Ogawa, et al.
U.S. Appl. No. 10/548,442, filed Aug. 18, 2004, Shiotsuka, et al.
U.S. Appl. No. 12/065,720, filed Oct. 3, 2006, Ban, et al.

Byun, et al., "Investigation of the Sensitivity Enhancement of Nanowire-Based Surface Plasmon Resonance Biosensors", The 13th International Conference on Solid-State Sensors, Actuators and Microsystems, Seoul, Korea, Jun. 5-9, 2005, pp. 1796-1799.

* cited by examiner

DETECTING ELEMENT, AND TARGET SUBSTANCE DETECTING DEVICE AND METHOD OF DETECTING TARGET SUBSTANCE USING THE SAME

TECHNICAL FIELD

The present invention relates to a detecting element which is used for a detecting device for detecting a target substance in a sample by utilizing plasmon resonance, to the detecting device and to a method of detecting a target substance.

BACKGROUND ART

Biosensors are measurement devices which utilize an excellent molecular recognizing ability of organisms or biomolecules. Combinations of biological substances which have affinity each other include, for example, enzyme-substrate, antigen-antibody, DNA-DNA etc. Biosensors utilize the principle where one substance of the above respective combination which is immobilized or supported on a substrate is used, thereby making it possible to selectively measure the other substance. In recent years, biosensors are expected to have wide application not only in medical fields but also in environment, foods etc. In order to increase the applicable area thereof, there is a need for small, light and highly sensitive biosensors which can be placed in any location or is portable.

Currently, as one of the highly sensitive sensing methods, plasmon sensors which utilize an interaction between existing plasmons of a metal surface or metal microparticles and light have been vigorously studied.

Sensors using conventional surface plasmon resonance (SPR (Surface Plasmon Resonance) sensors) utilize a phenomenon where the only light entered from a specific angle resonance with metal surface plasmons and is absorbed when the light is entered into a metal thin layer surface. The angle at which this absorbance occurs is sensitive to the surface condition of a metal thin layer (refraction index), and a reaction which occurs at a metal surface (e.g. antigen-antibody reaction) etc. can be measured by measuring an intensity of reflected light while changing an angle of incidence.

However, these SPR sensors require a prism in the construction, hence are complex in optics system. Therefore, it is considered that there is a limitation for miniaturization.

Japanese Patent Application Laid-Open No. 2000-035685 discloses a sensor which utilizes localized plasmon resonance by metal microparticles. The sensor disclosed in Japanese Patent Application Laid-Open No. 2000-035685 is a localized surface plasmon resonance (LSPR) sensor which detects a refraction index of a medium in the vicinity of metal microparticles by measuring an absorbance of light which passes through metal microparticles immobilized as a film on a substrate surface. It is considered that this sensor unit does not require a prism, can be placed at narrow spaces and can be applied on a substrate having a curved surface.

In J. Phys. Chem. B, vol. 103, p. 3073 (1999), nanorods are prepared by using gold. It discloses spectra based on localized plasmon resonance for these nanorods, and the relationship between an aspect ratio and a spectrum of nanorods is discussed therein.

In Japanese Patent Application Laid-Open No. 2000-035685, gold microparticles are immobilized on a surface-treated substrate by soaking the substrate in a solution of gold collides having a diameter of about 20 nm. The shape of gold microparticles may be close to the spherical shape. The fact is that enough sensitivity is not necessarily obtained with a plasmon sensor merely using these gold microparticles.

J. Phys. Chem. B, vol. 103, p. 3073 (1999) also discloses that the maximum absorbance wavelength is changed by making gold into a rod shape (columnar shape) and varying an aspect ratio of gold rods. However, J. Phys. Chem. B, vol. 103, p. 3073 (1999) does not disclose about orientation of gold rods and further improvement in the sensitivity is desired.

DISCLOSURE OF THE INVENTION

A detecting element provided by the present invention is the detecting element used for a detecting device for detecting a target substance in a sample by utilizing plasmon resonance, characterized in that it comprises a substrate and a plurality of metal members provided on the substrate, the metal member constituting a columnar structure and the columnar structure provided being oriented in a long axis direction thereof.

A detecting device provided by the present invention is the detecting device for detecting a target substance in a sample by utilizing plasmon resonance, characterized in that it comprises a detecting element for obtaining information of the target substance in the sample by being contacted with the sample, a light source for irradiating light to the detecting element and a light receiving element for receiving the light irradiated by the light source via the detecting element, the detecting element being the detecting element defined in the present invention.

A method of detecting a target substance provided by the present invention is the method of detecting the target substance in a sample by utilizing plasmon resonance, characterized in that it comprises steps of contacting the detecting element defined in the present invention with the sample, irradiating light to the detecting element, and receiving light obtained via the detecting element.

Further features of the present invention will become apparent from the following description of exemplary embodiments with reference to the attached drawings.

BEST MODES FOR CARRYING OUT THE INVENTION

The detecting element of the present invention is the detecting element used for a detecting device for detecting a target substance in a sample by utilizing plasmon resonance, characterized in that it comprises a substrate and a plurality of metal members provided on the substrate, said metal member constituting a columnar structure and said columnar structure provided being oriented in a long axis direction. Preferable embodiments of the present invention are illustrated in below.

(Columnar Structure)

Figure 1:
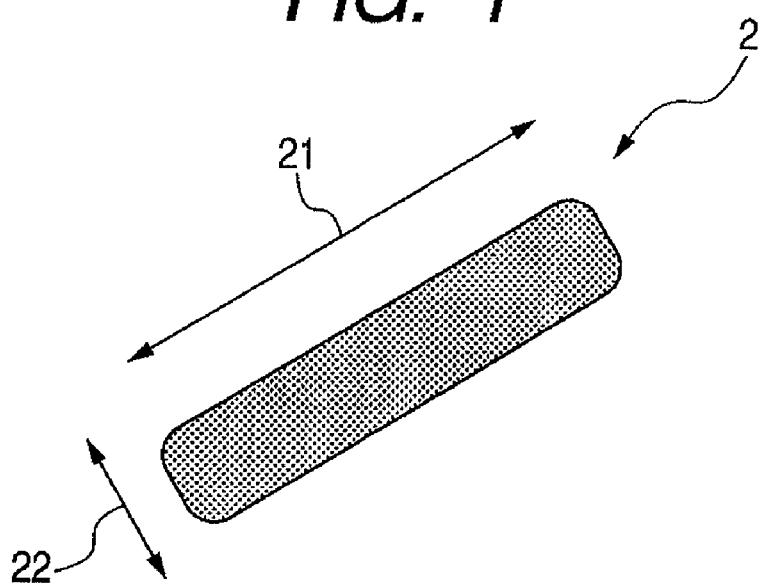
FIG. 1 is a schematic diagram which shows a shape of the columnar structure according to the present invention.
Figure 2:
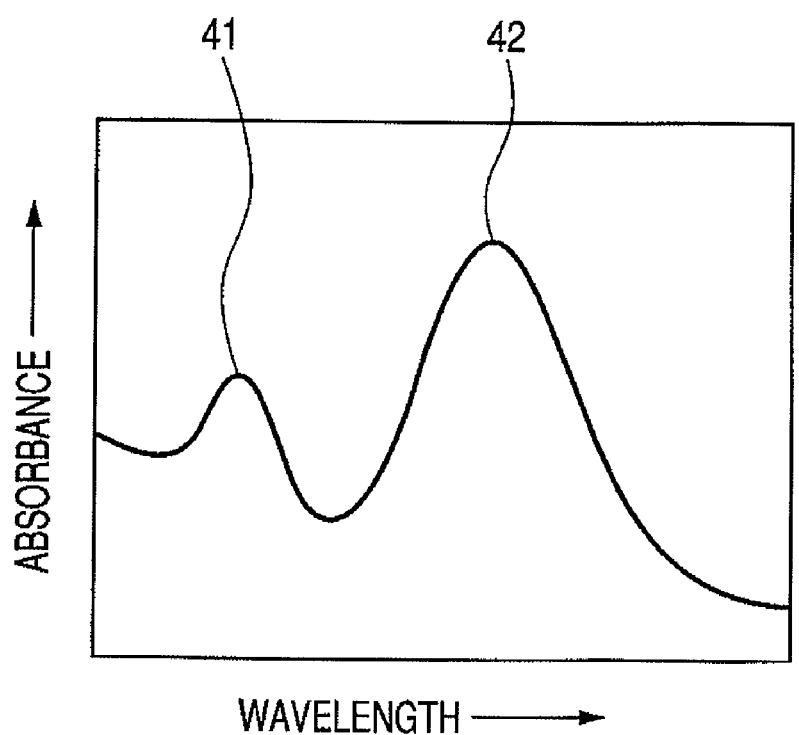
FIG. 2 is a schematic diagram which shows an example of an absorbance spectrum of the columnar structure having short and long axis directions.

The columnar structure according to the present invention has columnar shape of which lengths in a short axis direction 22 and long axis direction 21 are different as shown in FIG. 1. The columnar structure 2 is generally composed of metal microparticles. Being different from spherical metal particles, the columnar structure composed of metal particles provides an absorbance spectrum as shown in FIG. 2 because plasmon resonance frequencies of short and long axis directions are different. An absorbance in the short wave length side comprising a peak 41 in this spectrum is obtained due to plasmon resonance of the short axis direction of the columnar structure, and an absorbance in the long wave length side is obtained due to plasmon resonance of the long axis direction of the columnar structure. An absorption peak 42 in the long wave length side is easily affected by the refractive index change in the vicinity of the metal structure and has large amount of shift at the time of the refractive index change. The present invention is the one utilizing this phenomena; it provides the detecting element which makes it possible to detect the change highly sensitively in a property (refractive index) in the vicinity of the metal structure by irradiating light to the detecting element and detecting a property of light refracted from or passed through the detecting element. Thus, in the detecting element of the present invention, the columnar structure having short and long axis directions, and by effectively utilizing above-mentioned resonance of the long axis direction, enough sensitivity as detecting elements can be obtained.

The columnar metal structure can be referred to as a rod-shaped structure.

The material which composes the columnar structure may contain metal which can provide plasmon resonance phenomena. Such metal preferably includes gold, silver and copper. Silver is suitably used due to its high sensitivity notwithstanding its low corrosion resistance. Gold can provide a detecting element having high corrosion resistance and stability and has such advantage that it is easily modified in its surface with thiol etc.; thus gold is suitably used.

Metal particles which compose the columnar structure can be prepared by mixing a solution containing metal source such as gold chloride etc. with an additive such as a surfactant etc. or a pH-adjusting agent etc., and reducing the same. Such a preparation method can be applied to the present invention. The columnar structure according to the present invention can also be formed by, following the formation of a metal film, carrying out patterning.

The shape of the columnar structure may generally include, but not limited to, a cylindrical shape or a columnar shape in which the shape of the surface parallel with the short axis direction is rectangle, the short axis direction being perpendicular to the long axis direction.

With regard to the size of the columnar structure, a diameter or a side length of the short axis direction can preferably be in the range of 10 nm or more and 300 nm or less, more preferably of 20 nm or more and 200 nm or less. A length of the long axis direction of the columnar structure can be in the range of 20 nm or more and 3000 nm or less, more preferably of 40 nm or more and 2000 nm or less. In consideration of an absorbance peak and amount of the shift of plasmon resonance wave length, it is preferable that b/a is in the range of 2 or more and 10 or less, provided that a and b are the lengths in short and long axis directions, respectively.

(Orientation of the Columnar Structure)

As described above, sensitivity of the detecting element can be increased by effectively utilizing resonance of the long axis direction of the columnar structure using the metal member. According to the present invention, the columnar structures are provided with orientation on the substrate.

Figure 3:
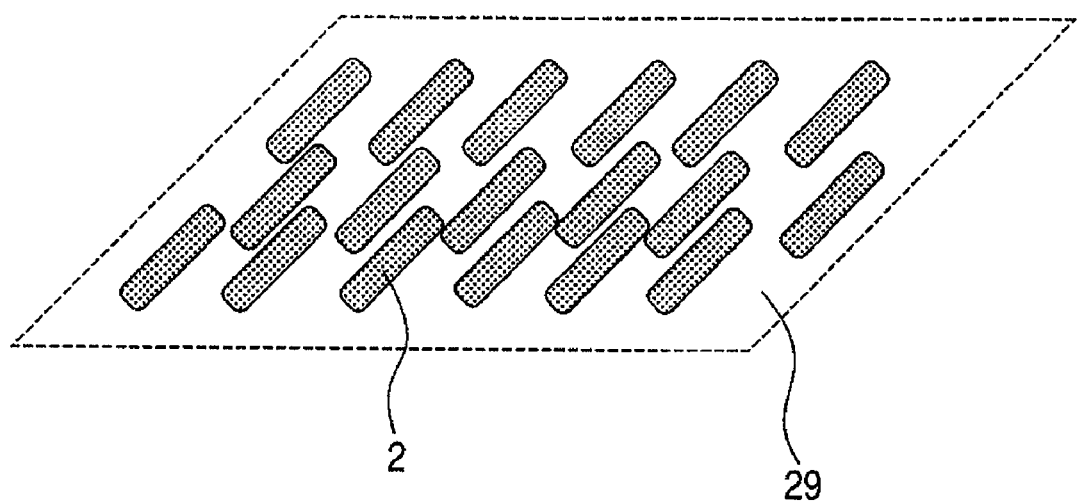
FIG. 3 is a schematic diagram which shows an example of an array having a selective orientation.

The orientation according to the present invention is described below with referring to the figures. FIG. 3 is an illustration using a virtual plane (a plane not necessarily be consistent with the surface of the substrate) 29. Reference numeral 2 shown in FIG. 3 denotes the columnar structure. As shown in FIG. 3, the long axis direction of the metal particles must be uniaxially oriented relative to the virtual plane. When light comprises a component which is irradiated perpendicularly to the virtual plane and when measured light (incident light) which enters the metal particle comprises a component parallel with the long axis direction of the columnar structure, resonance of the long axis direction of the columnar structure can be effectively utilized. By aligning a polarization direction of incident light to the long axis direction of the columnar structure, efficiency can be further increased.

The detecting element comprising a substrate in which the columnar structures are provided with orientation is now described.

Figure 4:
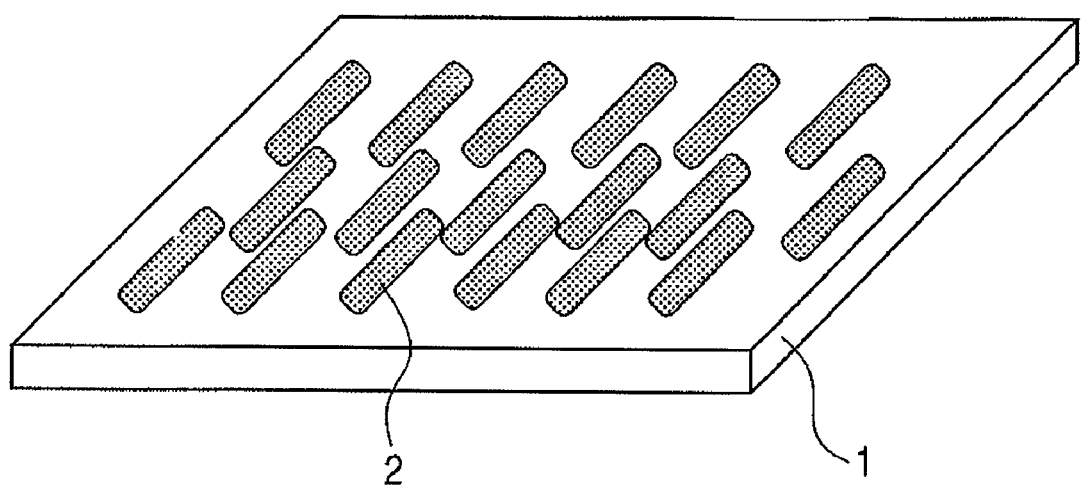
FIG. 4 is a schematic diagram which shows an example in which the long axis directions of the columnar structures are uniaxially oriented relative to the substrate.

FIGS. 4 and 5A, 5B and 5C are schematic diagrams which show examples in which the columnar structures are supported on the substrate in an array having a selective orientation. FIG. 4 shows an example in which the long axis direction of the columnar structure 2 is uniaxially oriented in parallel with the substrate 1. This orientation can be obtained with such method that a groove for immobilizing the columnar structures on the substrate is provided. The columnar structures can be provided with orientation by patterning the metal film.

Figure 5A:
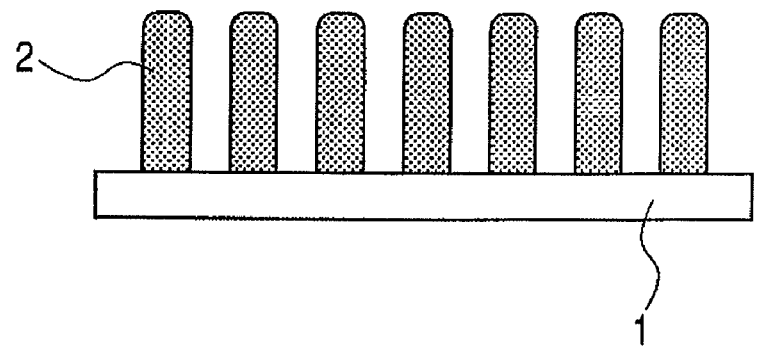
FIGS. 5A, 5B and 5C are schematic cross sectional diagrams which show examples in which the columnar structures are supported on the substrate with an array having a selective orientation.
Figure 5B:
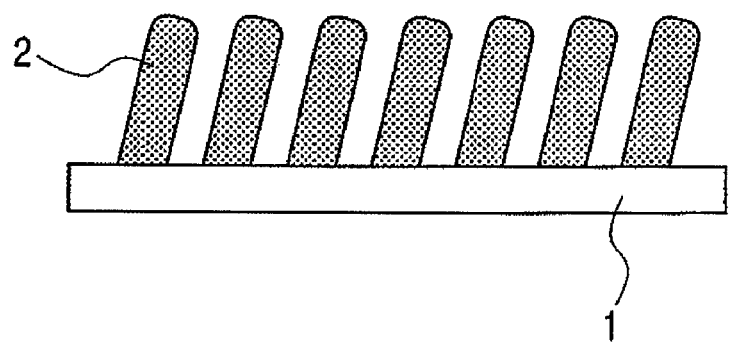
Figure 5C:
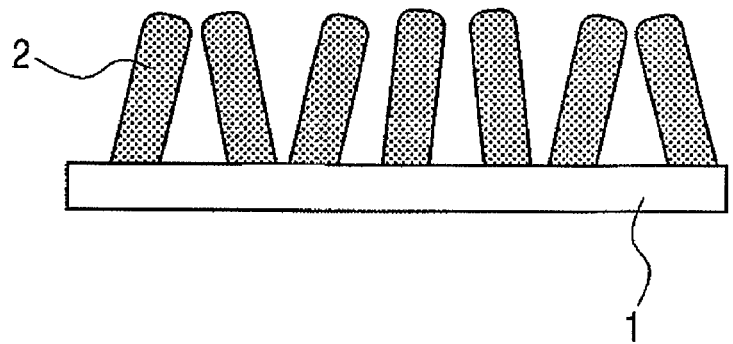

FIG. 5A shows an example in which the columnar structure 2 is selectively oriented approximately perpendicular to the substrate 1. This array can be formed by a method of preparing the columnar structures by contacting a porous body to be a template on the substrate, as described below for the method of preparation. Even with the array shown in FIG. 5B, the effect can be obtained because long axis directions of the columnar structures 2 are parallel and oriented uniaxially. Even with the orientation shown in FIG. 5C, the columnar structures 2 are approximately oriented in the long axis direction and the effect can be obtained. Thus, the orientation such as FIG. 5C is comprised in the case in which the columnar structures are oriented in the long axis direction. Among these, an embodiment in which long axis directions of the columnar structures are parallel as shown in FIGS. 5A and 5B is preferred. When the array such as FIG. 5A and the array such as FIG. 5B are compared, the case where the long axis direction of the columnar structures is perpendicular to the substrate as in FIG. 5A has more compatibility with the case where incidence light is perpendicular to the substrate.

When the long axis of the columnar structure is not completely uniaxially oriented as in FIG. 5C, an angle made with long axes of the respective columnar structures is preferably within 30°, and more preferably within 15°. This applies when the long axes of the columnar structures are oriented parallel with the substrate.

The shape, material etc. of the substrate may not be particularly limited so far as it can suitably support the columnar structures, and the substrate made of conventional materials such as inorganic materials such as resin, glass, silicon, etc., metal, metal oxide etc. can be used. When light which passes through the columnar structures and then the substrate is used for detection as transmitted light from the detecting element, the material of the substrate is preferably transparent to the wavelength of incident light and light to be detected. It is also possible to use light which passes through the columnar structure and then is reflected by the substrate can be used for detection as reflected light from the detecting element. In this case, it is preferable to use the substrate made of the material which reflects the wavelengths of incident light and light to be detected as a substrate.

In order to firmly support the columnar structures made of metal, it is preferable that a functional group having high affinity to metal such as an amino group or thiol group is formed on the substrate surface.

(Capturing Body Component)

The detecting element of the present invention preferably comprises a capturing body component which captures the target substance in the sample on the surface of the columnar structure made of metal.

The capturing body component used is a substance involved in the selection of the target substance in the sample. For example, a substance which selectively and directly reacts with the target substance in the sample (so called receptor), a substance which is involved in a reaction of the target substance (e.g. a substance which selectively provides a catalytic action to the reaction of the target substance), a substance which inactivates substances other than the target material in the sample, etc. are included. This capturing body component may also serve a function involved in the presentation of the presence or absence or an extent of the detection, such as a function of reacting with a substance released by receptors or a residual substance and developing a color, etc. The capturing body component used in the present invention includes, but not limited to, enzymes, sugar chains, catalysts, antibodies, antigens, genes, color reagents, etc.

The immobilization or support of these capturing body components on the surface of the metal structure is now explained.

The above-mentioned capturing body component is immobilized or supported on the surface of the metal structure by, for example, a covalent bond, ionic bond, adsorption, etc. However, the method for immobilization or support is not limited to these so far as this component is properly fixed or supported.

In a mode of binding, the capturing body component having a reactive group which can directly act on the surface of the metal structure may be directly reacted to bind, or a cross-linking material which can directly act on the surface of the metal structure may be reacted, and then the capturing body component may be reacted with the cross-linking material to bind. When the metal structure comprises, for example, gold or silver or copper, the capturing body component having a thiol or amino group, etc., can be directly immobilized. The capturing body component can be supported by allowing to react with a cross-linking material having a thiol or amino group, etc. such as a silane coupling agent etc. and then allowing the capturing body component to bind to the silane coupling agent.

In a mode of adsorption, a combination between materials of the capturing body component and the metal structure may be selected so as to have a suitable affinity. It is also possible to form a surface having a suitable affinity and immobilize the capturing body component by modifying the surface of the metal structure before hand.

(Detecting Device)

The detecting device of the present invention is now described.

The detecting device of the present invention is the detecting device for detecting a target substance in a sample by utilizing plasmon resonance, which comprises a detecting element for obtaining information of the target substance in the sample by being contacted with the sample, a light source for irradiating light to the detecting element and a light receiving element for receiving the light irradiated by the light source via the detecting element, the detecting element being the detecting element of the present invention.

As described above, in the detecting element of the present invention, the metal member constitutes the columnar structure, and the columnar structures are oriented in the long axis direction. Therefore, by irradiating light which comprises a component being parallel with the long axis direction of the columnar structures to the detecting element, it becomes possible to generate plasmon resonance due to the long axis direction of the columnar structure. It is preferable that light irradiated from the light source is irradiated to the detecting element as a polarized light having only a component of a direction of oscillation of an electric field parallel with the long axis direction of the columnar structure, as resonance in long axis direction can mainly be used. However, light comprising a component in which the direction of oscillation of the electric field is parallel can be used even if it is not polarized.

The light receiving element detects a property of light which is reflected by or passed through the detecting element. Therefore, it is provided at the position where it can preferably detect the light.

(Detection Method)

According to the detection method of the present invention, the property in the vicinity of the metal columnar structures is changed by the step of contacting the detecting element of the present invention with the sample including the target substance. When the detecting element comprises the capturing body component, a specific reaction between the capturing body component and the target substance occurs on the surface of the detecting element and then the property in the vicinity of the columnar structure changes. Then, light is irradiated to the detecting element which is composed of the columnar structure provided in the long axis direction. This step comprises a step of irradiating to the columnar structure light which contains a component parallel with the long axis direction of the columnar structure. Further, it becomes possible to receive light passed through or reflected from the detecting element, and to detect a change of the property in the vicinity of the metal structure. According to the present invention, it becomes possible to effectively use resonance in the long axis direction of the columnar structure and to carry out a highly sensitive detection by irradiating light having a component parallel with the long axis direction of the columnar structure. When the long axis directions of the columnar structures are not oriented completely uniaxially, the phrase "irradiating light having a component parallel with the long axis direction of the columnar structure" means irradiating light having a component which is parallel with any of the long axis directions of the plurality of the columnar structures. In such case, it is preferable to adjust incident light so that the sum of resonances in the long axis directions of the columnar structures is maximum.

A subject of measurement of the detecting element, detecting device, and detection method of the present invention may not necessary be a target substance which directly reacts with the capturing component, i.e., it may be measured indirectly. For example, the measurement is possible by detecting the target substance specifically exists in the subject of measurement. Therefore, the subject of measurement is not limited to biological substances and the size thereof is not limited. The target substance is preferably a biological substance contained in organisms such as saccharides, proteins, amino acids, antibodies, antigens and pseudo-antigens, vitamins, genes, etc., and other related substance or artificial biological substance which is synthesized artificially.

The capturing body component can be used in combination, and it is possible to compose the detection apparatus such as a combined enzyme sensor, antibody-enzyme sensor, enzyme-microbial hybrid sensor, etc.

The method of producing the detecting element of the present invention is now described.

For example, the detecting element can be produced by carrying out the following steps (A) to (D).

Step (A): step of preparing porous body having columnar pores

In this step, a porous body having columnar pores is prepared.

Materials, size, shape, etc. of the porous body is not limited so far as pores thereof can be templates for the formation of metal particles, and the porous body to be used can, for example, be the one in which pores are provided by processing such as etching etc. on an optional substrate or film. Alternatively, anodic oxidized alumina which is formed on the surface of aluminum by anodic oxidation of aluminum in an acidic electrolyte has columnar pores, thus it is preferably used. As the diameter or depth of pores of anodic oxidized alumina can be relatively freely controlled, the use thereof is preferable for the control of the shape or size of the metal particles. A membrane filter of polycarbonate also contains columnar pores and is commercially available, thus is conveniently used.

Step (B): step of introducing metal into pores of porous body

In this step, the porous body is used as a template, and materials of the metal particles are introduced into the pores.

Introduction of materials of the metal particles into the pores of the porous body can be carried out by vapor deposition, sputtering, metal plating, etc. However, a method of introduction is not limited to these methods so far as materials of the metal particles can be introduced into the pores of the porous body. A metal plating method is preferably used because the amount of metal particle materials to be introduced can be controlled by changing the processing time. By increasing the processing time, as shown in FIG. 6A, the metal material 63 is filled into the pores 62 of the porous body 61, and with the step (C) described below, the metal columnar structure is formed. In this figure, reference numeral 65 denotes a layer of the metal material which is formed between porous body 61 and a base plate on which it is set.

Step (C): Step of removing porous body and preparing columnar structure

A method of removing the porous body is not limited so far as the porous body can selectively be removed and the columnar body can be obtained. According to the present invention, an etching technique is preferably used because it is convenient and applicable to various materials. For example, when anodic oxidized alumina is used for the porous body, alumina can be removed by etching with hydrogen fluoride, sulfuric acid or a mixture of phosphoric acid and chromic acid, etc. By selectively removing the porous body as above, the metal columnar body as shown in the schematic diagram of FIG. 1 can be obtained.

Figure 6:
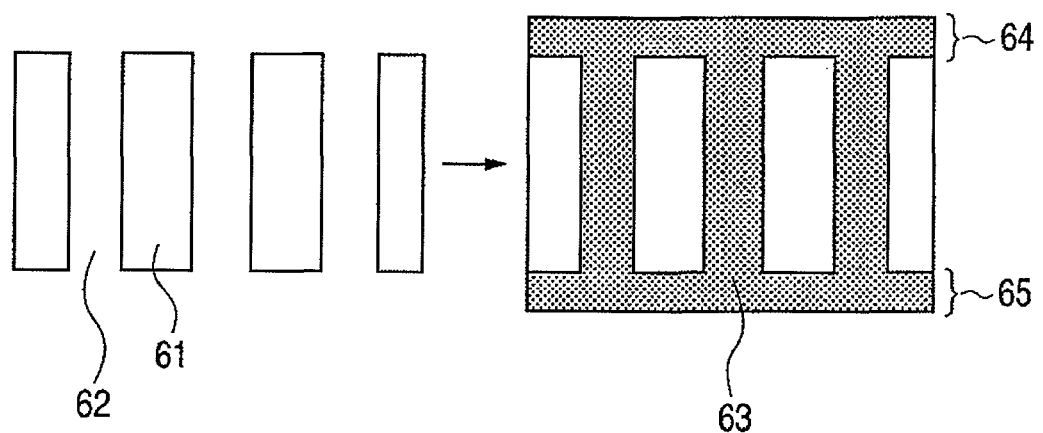
FIG. 6 is a schematic diagram which shows a process of forming the columnar structures.

When, in the above step (B), a metal material layer 64 is formed on the surface of the porous body 61 as shown in FIG. 6, an etching treatment may be carried out after removing the metal material layer 64 by polishing, etc., in order to increase an efficacy of the etching of the porous body and to increase the uniformity of the shape of the metal formed.

Step (D): Step of supporting columnar structures on substrate in an array having selective orientation The columnar structures prepared in the above steps (A) to (C) are dispersed in a solution to obtain a dispersed solution. The substrate is soaked in the dispersed solution, or the dispersed solution is applied on the substrate. If grooves are formed on the substrate in a uniaxially oriented array, the columnar structures may be supported in a uniaxially oriented array. Thereby, the columnar structures are supported on the substrate with the long axis direction of the metal structure being uniaxially oriented as shown in FIG. 4. When dip-coating technique is used as an application method and the application is carried out such that the direction of drawing of the substrate and the direction of the grooves are aligned, the columnar structures can be supported in an array having higher extent of uniaxial orientation. It is preferable to carry out a surface treatment to the substrate in advance to improve an affinity between the columnar structures and the substrate surface in order to maintain the columnar structures firmly. For example, when the columnar structures contain gold, it is preferable to form a functional group such as an amino or thiol group on the substrate surface. Excess columnar structures may be removed by washing the substrate with solvent, etc.

In the case where the columnar structures are to be aligned in an array having the selective orientation as shown in FIGS. 5A, 5B and 5C, the columnar structures can be prepared by immobilizing the porous body on the substrate.

Figure 7:
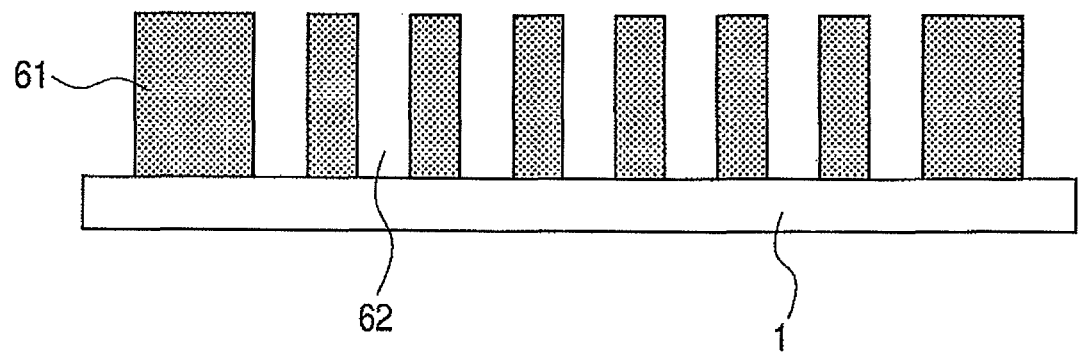
FIG. 7 is a schematic diagram which shows an example of a porous body immobilized on the substrate.

The metal structures in an array having the selective orientation as shown in FIGS. 5A, 5B and 5C can be aligned on the substrate by fixing porous bodies 61 prepared in the above step (A) on the substrate 1 as shown in FIG. 7, and then carrying out the steps (B) and (C). By varying shapes of pores 62 of the porous body used, or the position, angle, etc of immobilization of the porous body to the substrate, the columnar structures can be formed in an array selectively oriented almost perpendicular to the substrate as shown in FIG. 5A, or in a desired array as shown in FIGS. 5B and 5C.

The detecting element of the present invention can be prepared by carrying out the above steps (A) to (D). Alternatively, the columnar structures can be formed by patterning a metal film.

EXAMPLES

The present invention is further illustrated by the following Examples. However, the present invention is not limited to these Examples and materials, formulation conditions, reaction conditions, etc. can be freely modified in such extent that the detecting elements and device having similar functions and effects are obtained.

Example 1 and Comparative Example 1

The present Example shows an example of the preparation of the detecting element by preparing columnar structures consisting of gold and supporting the columnar structures on a substrate in an array in which the substrate and a long axis direction of the columnar structures are selectively oriented approximately in a uniaxial direction. In this Example, a detecting device comprising the detecting element was further produced and the detection of a target substance was carried out.

When the columnar structures consisting of metal are selectively oriented in a uniaxial direction and supported on the substrate as the present Example, light irradiated from a light source can be a polarized light such that a direction of oscillation of a component of an electric field is parallel with the long axis direction of the columnar structure. By using this, an absorption peak in the short wavelength side in FIG. 2 can be decreased and an absorption peak in the long wave length side can be detected more definitely.

First, an aluminum substrate was prepared and washed with pure water and isopropyl alcohol. The aluminum substrate washed is subjected to an anodic oxidation at 40V in a solution of 0.3 M oxalic acid, then the aluminum surface can be oxidized to alumina, and simultaneously, columnar pores are formed to obtain a porous body. Immersing the porous body in 5 wt % of phosphoric acid for a determined period of time can increase a diameter of pores and makes it possible to obtain the porous body having a desired pore size. It is possible to change intervals between pores by changing the type of the acid used for the anodic oxidation. It is possible to form columnar pores having, for example, a diameter of 40 nm and a length of 120 nm by controlling the conditions.

Then, gold is introduced in the pores of the porous body by nonelectrolytic plating. The porous body is then immersed in 5 wt % of phosphoric acid in order to selectively dissolve and remove the porous body to obtain columnar structures. The columnar structures are isolated from the solution by centrifugation, followed by washing. The thus-obtained columnar structures have a diameter of 40 nm and a length of the order of 120 nm. The obtained columnar structures are dispersed in a solution containing a dispersing agent to obtain a dispersant in which the columnar structures are dispersed.

Next, a quartz substrate is prepared as a substrate for the detecting element, and a plurality of linear grooves are formed on the substrate surface by using a technique of photo lithography. The width of the groove is the order of 100 nm. Then, amino groups are formed on the surface of the substrate by using an amino silane coupling agent. The dispersant in which the columnar structures are dispersed is applied on the quartz substrate by a dip-coating technique.

It is preferable to draw the substrate in the same direction as that of the grooves.

After the above process, the quartz substrate on which the columnar structures are oriented in the long axis direction as shown in FIG. 4 can be obtained.

Then, an antibody as a capturing body component is immobilized on the surface of the columnar structures consisting of gold. In this Example, anti-AFP (a-fetoprotein) antibody is used as an antibody.

First, the columnar structures are modified on the surface with 11-mercaptoundecanoic acid to form carboxyl groups on the surface. Then, an aqueous solution of N-hydroxysulfosuccinimide (manufactured by Dojindo Laboratories) and an aqueous solution of 1-ethyl-3-[3-dimethylamino]propyl] carbodiimide hydrochloride (manufactured by Dojindo Laboratories) are applied to expose succinimide groups on the surface of the columnar structures. Further, streptoavidine is bound to modify the surface of the columnar structures with streptoavidine. Then, biotinylated anti-AFP antibody is immobilized on the columnar structures.

After the above process, the detecting element having anti-AFP antibody as a capturing body component can be prepared.

Now, an example of a detecting device comprising the detecting element prepared by the above procedure is described. This Example shows an example in which detection is carried out with light passed through the detecting element.

Figure 8A:
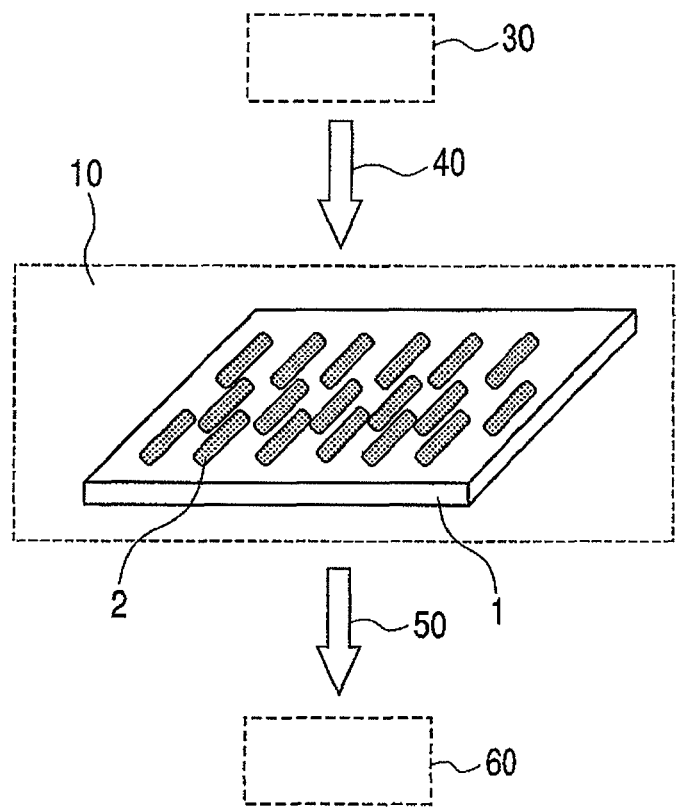
FIGS. 8A and 8B are schematic diagrams which show examples of the detecting device of the present invention.

FIG. 8A is a diagram which schematically shows the detecting device according to the present Example. The detecting device comprises a light receiving element 60 and a light source unit 30 which irradiates measured light 40 to the detecting element 10. The light source unit 30 also comprises a polariscope which is not shown in the figure. The light source and polariscope are provided such that a direction of oscillation of a component of the electric field of the measured light polarized by the polariscope and a long axis direction of the columnar structure 2 in the detecting element 10 are parallel. The position of the light receiving element 60 is such that it can detect a property of measured light 50 which passes through the detecting element 10. The light receiving element may further comprise a spectral detector which is not shown in the figure. A computer which computes detected property changes, a displaying means which displays detection results, etc., which are not shown in the figure are preferably comprised.

Figure 8B:
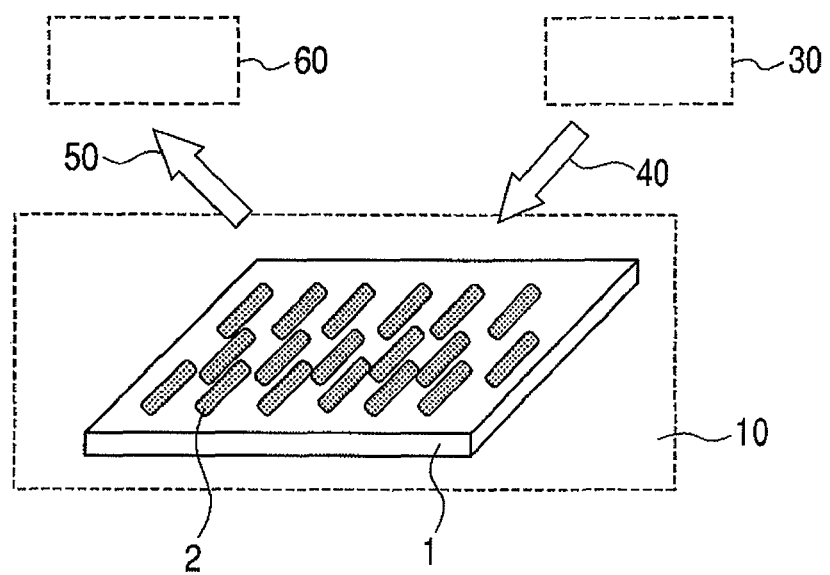

In the above, the detecting device of transparent type is described. However, positions of the light source 30 and light receiving element 60 shown in FIG. 8A can be changed to those shown in FIG. 8B to obtain the detecting device of reflective type which receives light 50 reflected by the detecting element 10 with the light receiving element 60.

Now, an example of a detection method using the obtained detecting device is described.

First, the detecting element, light source and light receiving element are provided in relative positions at the time of detecting a target substance, and then a spectrum is measured. Then, a sample consisting of a phosphate buffer solution containing AFP as a target substance is added on the substrate, is allowed to contact with the detecting element and then is reacted with the capturing body component. After the reaction, washing may be carried out with the phosphate buffer solution. Thereafter, the detecting element, light source and light receiving element are provided in relative positions as the above time of detection, and a spectrum is measured. The change in a spectrum before and after addition of the sample is derived from the change in a state of localized plasmon resonance of the columnar structures and it means that antigen-antibody reaction occurs on the detecting element and that the target substance is captured by the capturing body component.

With regard to the relation between the change in a spectrum and the concentration of the target substance, such relation between the change in a spectrum and the concentration is obtained beforehand by using standard samples with various known concentrations; based on this relation, a calibration curve is obtained and then a function between the change in a spectrum and the concentration is obtained. With this function, the concentration of the target substance can be obtained by the actual measured change in a spectrum.

The change in a spectrum may be the change in a spectrum peak at the wavelength of a maximum value, or may be the change in a peak shape such as a half-value breadth of a waveform of a spectrum peak. Alternatively, a light intensity at one or more wavelength points may be used.

The case where the detecting element of the present Example in which the long axis direction of the columnar structures is oriented along grooves formed on the substrate surface and polarized light as a irradiated light were used, and the case where the columnar structures are provided randomly without making grooves on the substrate surface (random arrangement) were compared. Thus, the peak intensity of resonance wavelength of the long wavelength side for the present Example was approximately 1.5 times higher than that of the random arrangement, and the absorption peak itself for the present Example was steep and easily identified. When the use of polarized light is compared with the use of non-polarized light for the detecting element of the present Example, the absorption peak intensity of the long wavelength side for the use of non-polarized light was decreased compared to that for the use of polarized light, whereas identification of the shift of resonance peak was not interfered.

As described above, the present invention makes it possible to detect the target substance in the sample with sufficient sensitivity.

Example 2

The present Example shows an example of the preparation of the detecting element by preparing columnar structures consisting of gold, allowing a substrate and the long axis direction of the columnar structures to be oriented in approximately perpendicular, and providing the substrate in a pass. A detecting device composed of the detecting element and the continuous detection of a target substance using the detecting device are also described.

The present invention can be applied to the detection of a target substance flowing in a pass, thus the detecting device can be prepared in a form of a microchip. The reaction efficiency between the capturing body component and the target substance can be improved by providing many columnar structures in the pass.

First, the porous body is prepared by the same method as Example 1. Second, the porous body is brought into intimate contact with the area where a pass will be provided on the glass substrate and is immobilized. Then, the area other than the area which will be a reactive area is masked and gold is introduced in pores of the porous body on the reactive area by nonelectrolytic plating. Thereafter, it is immersed in 5 wt % sulfuric acid and the porous body is dissolved and removed to obtain the columnar structures consisting of gold on the substrate, as shown in FIG. 5A.

Figure 9A:
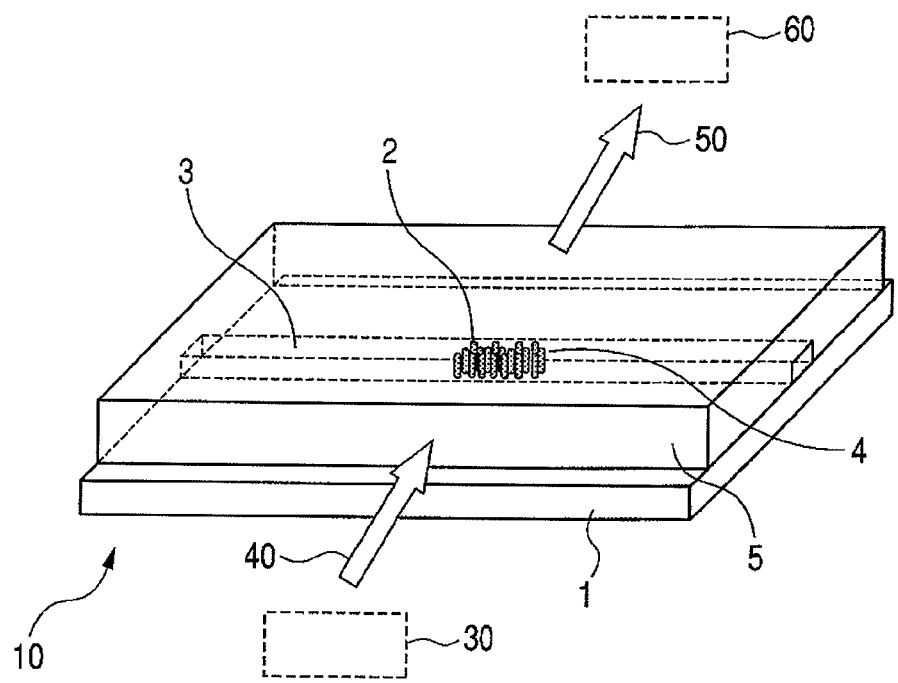
FIGS. 9A and 9B are schematic diagrams which show examples of the detecting device of the present invention.

A resin cover provided with a groove is immobilized on the glass substrate to prepare a pass. As shown in FIG. 9A, the cover 5, the substrate 1 and the reactive area 4 are provided such that the reactive area 4 in which columnar structures 2 of metal are formed in the pass 3 is provided to prepare the detecting element.

Then, antibodies as a capturing body component are immobilized on the surface of columnar structures. In this Example, rabbit anti-mouse IgG antibodies are used as an antibody. Immobilization is carried out by successively feeding a solution of 11-mercaptoundecanoic acid in ethanol, an aqueous solution of N-hydroxysulfosuccinimide, 1-ethyl-3-[3-dimethylamino]propyl]carbodiimide hydrochloride, rabbit anti-mouse IgG antibody/Tris-HCl buffer solution in the pass.

After the above process, the detecting element having rabbit anti-mouse IgG antibodies as a capturing body component can be prepared.

Now, a detecting device comprising the detecting element prepared by the above procedure is described. This Example shows an example in which detection is carried out with light passed through the detecting element.

Figure 9B:
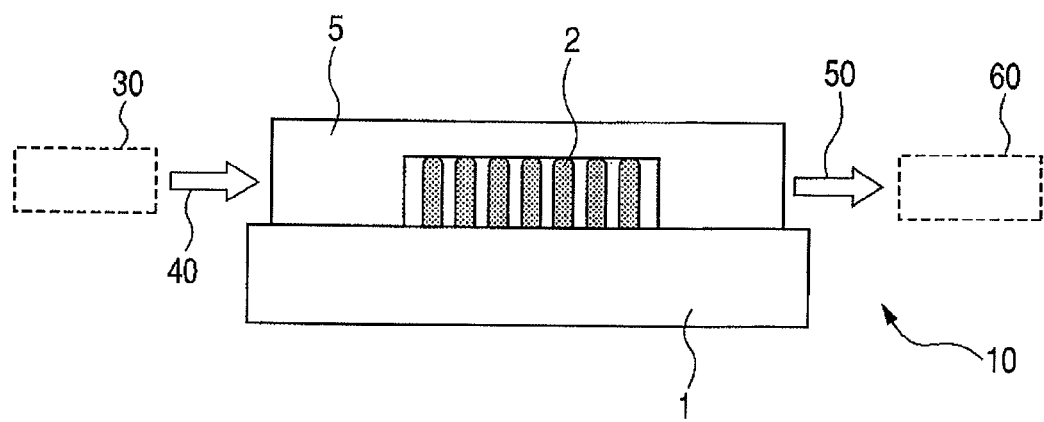

FIGS. 9A and 9B are diagrams which schematically show the detecting device according to the present Example. FIG. 9A is a perspective view and FIG. 9B is a section view. The detecting device comprises a light source 30 and a light receiving element 60 against the detecting element. Thus, the position of the light source 30 is such that it can irradiate measured light 40 which contains a component parallel with the long axis direction of the columnar structure 2 in the detecting element 10, as schematically shown in FIGS. 9A and 9B. The position of the light receiving element 60 is such that it can detect a property of measured light 50 which passes through the detecting element 10. The light receiving element 60 may further comprise a spectral detector which is not shown in the figure. A computer which computes detected property changes, a displaying means which displays detection results, a means for feeding a sample to the pass such as a pump etc., which are not shown in the figure are preferably provided.

Now, an example of a detection method using the obtained detecting device is described.

First, the detecting element, light source and light receiving element are provided in relative positions for detection as above, and then a spectrum is measured. Then, a sample consisting of a phosphate buffer solution containing mouse IgG is introduced and fed into the pass, is allowed to contact with the detecting element and then is reacted with the capturing body component. Thereafter, the detecting element, light source and light receiving element are provided in relative positions as the above time of detection, and a spectrum is measured. The change in a spectrum before and after addition of the sample is derived from the change in a state of plasmon resonance of the columnar structures and it means that antigen-antibody reaction occurs on the detecting element and that the target substance is captured by the capturing body component.

By obtaining the calibration curve as described in Example 1, the concentration of the target substance can be determined.

As in Example 1, the change in a spectrum may be the change in the wavelength of the spectrum peak, or may be the change in a spectrum peak shape. Alternatively, a light intensity at one or more wavelength points may be used.

It is possible to detect the change over time or the change in an amount of reaction by continuous detection while feeding a solution, because the detecting element is provided in the pass according to the present invention.

As shown above, the present invention makes it possible to detect a target substance in a sample with sufficient sensitivity.

According to the preferred Examples of the present invention, by providing a plurality of metal members constituting the columnar metal structures with an orientation in the long axis direction, resonance in the long axis direction can be effectively utilized and the amount of wavelength shift of plasmon resonance peak can be increased. According to this, sensitivity at the time of detection of the target substance utilizing plasmon resonance is improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-072587, filed Mar. 16, 2006, which is hereby incorporated by reference herein in its entirety.

The invention claimed is:

1. A detecting element used for a detecting device for detecting a target substance in a sample by utilizing plasmon resonance,
wherein the element comprises a pass and a plurality of metal members provided on at least one part of a wall surface comprised in the pass, the metal member constituting a columnar structure and the metal member being oriented in a long axis direction thereof, the long axis direction being perpendicular to the part of the wall surface.

2. The detecting element according to claim 1, wherein the orientation is such that the long axis direction of the columnar structure and a face of the substrate on which the columnar structure is provided are parallel.

3. The detecting element according to claim 1, wherein the orientation is such that the long axis direction of the columnar structure and a face of the substrate on which the columnar structure is provided are perpendicular.

4. The detecting element according to claim 1, wherein b/a is in the range of 2 or more and 10 or less, provided that a and b are the lengths of the columnar structure in short and long axis directions, respectively.

5. The detecting element according to claim 1, wherein a diameter or a side length of the columnar structure is in the range of 10 nm or more and 300 nm or less.

6. The detecting element according to claim 1, wherein the columnar structure has, on the surface thereof, a capturing body for capturing the target substance in the sample.

7. A target substance detecting device for detecting a target substance in a sample by utilizing plasmon resonance, wherein it comprises a detecting element for obtaining information of the target substance in the sample by being contacted with the sample, a light source for irradiating light to the detecting element and a light receiving element for receiving the light irradiated by the light source via the detecting element, the detecting element being the detecting element according to claim 1.

8. A method of detecting a target substance in a sample by utilizing plasmon resonance, wherein it comprises the steps of:
    contacting the detecting element according to claim 1 with the sample;
    irradiating light to the detecting element; and
    receiving light obtained via the detecting element.

9. The method of detecting a target substance according to claim 8, wherein the light-irradiating step is a step of irradiating a polarized light.

10. The method of detecting a target substance according to claim 8, wherein the polarized light is such that a direction of oscillation of a component of an electric field is parallel with the long axis direction of the columnar structure.

* * * * *